United States Patent
Tosch et al.

(10) Patent No.: US 8,238,698 B2
(45) Date of Patent: Aug. 7, 2012

(54) OPTICAL MEASURING PROBE FOR PROCESS MONITORING

(75) Inventors: Stephan Tosch, Sprockhövel (DE); Reinhard Gross, Leverkusen (DE); Marcus Brand, Dormagen (DE); Hans Tups, Bergisch Gladbach (DE)

(73) Assignee: Bayer Technology Services GmbH, Leverkusen (DE)

( * ) Notice: Subject to any disclaimer, the term of this patent is extended or adjusted under 35 U.S.C. 154(b) by 5 days.

(21) Appl. No.: 12/375,496

(22) PCT Filed: Jul. 20, 2007

(86) PCT No.: PCT/EP2007/006494
§ 371 (c)(1),
(2), (4) Date: Feb. 10, 2009

(87) PCT Pub. No.: WO2008/014901
PCT Pub. Date: Feb. 7, 2008

(65) Prior Publication Data
US 2009/0201493 A1 Aug. 13, 2009

(30) Foreign Application Priority Data
Aug. 2, 2006 (DE) .......................... 10 2006 035 996

(51) Int. Cl.
*G02B 6/00* (2006.01)
*G01N 21/00* (2006.01)
(52) U.S. Cl. .......................................... 385/12; 356/436
(58) Field of Classification Search ................ 385/12; 356/436
See application file for complete search history.

(56) References Cited

U.S. PATENT DOCUMENTS

| 3,970,394 | A | 7/1976 | Stanton |
| 2002/0041724 | A1* | 4/2002 | Ronnekleiv et al. ............. 385/12 |
| 2003/0090667 | A1 | 5/2003 | Kaufmann |
| 2005/0054900 | A1* | 3/2005 | Mawn et al. .................. 600/156 |

FOREIGN PATENT DOCUMENTS

| EP | 0336045 A1 | 12/1988 |
| JP | 2000-234953 A | 8/2000 |
| WO | 2005/003740 A1 | 1/2005 |

OTHER PUBLICATIONS

English Language Abstract for JP 2000-234953 A.
English Language Abstract for WO 2005/003740 A1.
Jörg-Peter Conzen, Tim Stadelmann: "Fibert Optic Probes for the Process Technology" 2004, BRUKER OPTIK GMBH, pp. 28-32.

* cited by examiner

*Primary Examiner* — Ryan Lepisto
*Assistant Examiner* — Jerry Blevins
(74) *Attorney, Agent, or Firm* — Norris McLaughlin & Marcus, P.A.

(57) ABSTRACT

The invention relates to an optical measurement probe for process monitoring, having a distal end, arranged in the region of a process apparatus, with a light entrance opening, and a proximal end coupled to a spectrometer, wherein a shaft comprising a light-guiding connection between the distal and proximal ends of the measurement probe is arranged between the two ends. The measurement probe is characterized in that the measurement probe has, in its distal region relative to the shaft and/or the proximal end, a reduced external diameter (FIG. 1).

4 Claims, 1 Drawing Sheet

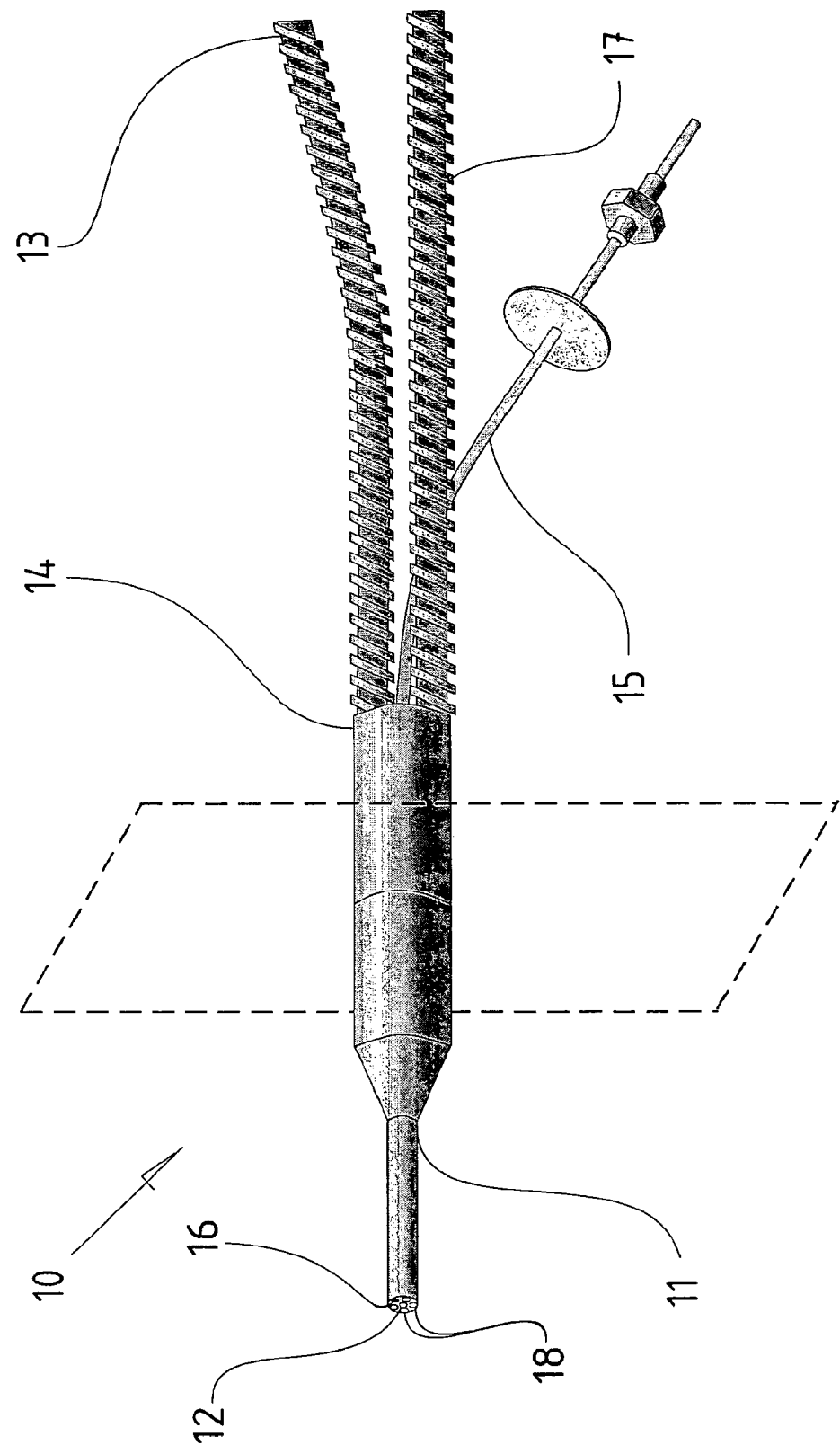

OPTICAL MEASURING PROBE FOR PROCESS MONITORING

This is an application filed under 35 USC §371 of PCT/EP2007/006494, claiming priority to DE 10 2006 035 996.8 filed on Apr. 2, 2006.

BACKGROUND OF THE INVENTION

The present invention relates to an optical measurement probe for process monitoring, in particular for reflection measurements on solids, emulsions and suspensions.

In the field of process apparatuses, optical measurement probes are frequently used to monitor processes in the process industry, in particular in the chemical, pharmaceutical and food industries. These measurement probes can be used to measure the concentration, material identity, turbidity and purity of starting materials, intermediate products and products (solids, emulsions and suspensions) in real time.

Optical measurement probes have the advantage that they operate without taking samples, enable the simultaneous determination of the concentrations of a plurality of analytes and can also be employed in unfavourable milieus (toxic, corrosive, radioactive, at risk of explosion, sterile, contaminated).

These probes are generally fibre-optic elements, whose distal ends, which have the light entrance opening, are arranged in the process apparatus, i.e. more or less near the analytes or in direct contact therewith, and whose proximal ends are coupled to an evaluation device, for example an NIR spectrometer.

These probes are generally used to carry out reflection measurements of the process material with the aid of a light source with a known spectrum, whose light is frequently coupled into the measurement site via a separate optical waveguide arranged in the measurement probe.

It is thus possible, for example, during the process control of polymer melts in the extrusion to quickly and reliably determine the exact chemical composition of a polymer melt in real time.

Time-consuming off-line analysis by taking samples can therefore be dispensed with.

Quite an accurate picture of the process conditions can thus be gathered by combining these measurement variables obtained by optical means with further measurement variables (temperature, pressure, pO2 etc.), not obtained by optical means, and it is possible to correctively intervene in the process in real time. Operational losses on account of production downtimes or malfunctions can be avoided in this manner.

Said systems comprise one or more fibre-optic measurement probes and an evaluation device, such as an NIR spectrometer, for example, and are available for example from Bayer under the trade name "Spectrobay". Another supplier is Sentronic.

Said measurement probes must be of very robust and resistant design at least in the region of their distal ends because of the extreme chemical, thermal and mechanical conditions prevailing in the said process apparatuses. They therefore generally have a fibre-optic core and flexible metallic reinforcement. In order to bring about the required stability, generic measurement probes currently on the market have a diameter of at least 8 mm, which extends up into the distal region of the measurement probe.

The main problem with such measurement probes is, however, their high sensitivity with respect to contaminations. Material from the process apparatus, for example, has a tendency to deposit on the light entrance opening at the distal end of the measurement probe and can thus corrupt the reflection measurements. Such corrupted measurements must be expected in particular if the light entrance opening is situated in a reduced-flow region of the process apparatus, that means if deposits, once they have formed, are not easily swept away again, and/or if the material in the process apparatus has thermoplastic properties and, once it has deposited on the light entrance opening, solidifies on account of cooling.

BRIEF SUMMARY OF THE INVENTION

It is therefore an object of the present invention to provide an optical measurement probe for the real-time process control in accordance with the above introduction, which is less susceptible to corruption of measured values caused by deposits and contaminations.

This object is achieved by virtue of the features of the present independent claims. The subclaims indicate preferred embodiments.

Accordingly, an optical measurement probe for process monitoring is provided, having a distal end, arranged in the region of a process apparatus, with a light entrance opening, and a proximal end coupled to an evaluation device.

The evaluation device can be, for example, a photometer or spectrometer, in particular a Fourier transformation NIR or IR spectrometer, a grating or AOTF spectrometer, or a spectrometer based on a CCD or a photodiode array. In particular in the case of fluorescence measurements, the evaluation device can also be, for example, a photomultiplier. The evaluation can extend from the UV into the IR range. The evaluation device can also be a Raman spectrometer.

A shaft comprising a light-guiding connection between the distal and proximal ends of the measurement probe is arranged between the two ends. The measurement probe has, in its distal region relative to the shaft and/or the proximal end, a reduced external diameter. A conical transition can be provided here between the shaft and the distal region of the measurement probe with reduced external diameter.

In this way, the measurement probe provides only a small area for the deposition of contaminations in the region of the process apparatus, and the forces which the moving process material has to exert in order to tear away again any adherent deposits are reduced to the lowest possible level.

By way of example, it may be provided that the distal region, arranged in the region of the process apparatus, of the measurement probe has an external diameter of 2 mm, while the shaft and the proximal region each have an external diameter of 12 mm. The area on which process material can deposit is thus reduced by a factor of 36 on account of the taper according to the invention.

In principle, an optical waveguide bundle has, besides the actual optical waveguides, a coating and generally flexible reinforcement. The latter two components are responsible for the mechanical stability, the flexibility and, where appropriate, the tightness of the optical waveguide bundle and contribute significantly to the external diameter of the optical waveguide bundle.

The measurement probe according to the invention dispenses with the flexible sheathing in its distal region and instead has in this region a rigid sleeve which tapers conically at least in sections, where appropriate. In this way it is possible to drastically reduce the external diameter of the measurement probe in this region without the need to accept losses in terms of mechanical stability, flexibility or tightness.

It is preferably provided that the measurement probe has a purging device with a purging duct arranged in the region of the shaft and with a purging opening arranged in the region of the distal end. The purging opening is preferably arranged next to the light entrance opening. This purging device can be used to remove, by purging, deposits which adhere despite the reduced area in the region of the distal end of the measurement probe.

Here, a coupling, which can be used to introduce the purging medium into the purging device, is provided in the region of the shaft or in the proximal region of the measurement probe.

Suitable purging media are liquids such as water or solvent, gases such as air or inert gases (N2, Ar, Xe), or conveyable solids such as powder or microgranules. The selection of the purging medium is dependent on the process conditions and the compatibility of the purging medium with the process material.

It is likewise possible to use as purging medium starting materials, intermediate products or products used in the relevant process. These can also be in liquid, gaseous or conveyable solid form. In this way it is possible, where appropriate, for the purging medium to be an integral and quantitatively integrated part of a process, in particular of a production process.

The purging device is designed with particular preference such that purging can be carried out continuously, at fixed intervals or if cleaning is required.

It is possible in the latter case that the measurement signal generated by the measurement probe and monitored by the evaluation device is used as an indicator for any possible contamination of the distal region of the measurement probe. For this purpose, provision can be made in particular for the conclusion to be drawn that a contamination is present and for a purging action to be initiated if there are rapid changes of the measurement signal which lie above a specific threshold value $\Delta S/t$. The purging device is preferably designed for this purpose such that purging takes place in a pulsed manner and/or with high pressure.

The light-guiding connection of the measurement probe according to the invention preferably involves optical waveguides or fibre-optic waveguide bundles. Fibre-optic waveguide bundles have been used for a fairly long time and are available in a wide variety of designs. It is possible, in particular, for the selection of the glass used for the fibres and for the arrangement of the fibres to be matched to the process conditions and the electromagnetic spectrum used.

It is particularly preferably provided that the measurement probe is designed for reflection measurements. This type of measurement method enables a non-destructive measurement which is in inline contact with the product. It can likewise be provided that the measurement probe is designed for fluorescence measurements and/or Raman measurements and also turbidity measurements.

In another embodiment of the measurement probe according to the invention, it is provided that the measurement probe has a further light-guiding connection for coupling in measurement light of a light source with a known spectrum and has a light exit opening in the distal region of the measurement probe. Here, the light exit opening in the region of the distal end of the measurement probe is preferably arranged next to the light entrance opening; frequently, a plurality of light exit openings are arranged around a light entrance opening which is arranged centrally.

This second light-guiding connection preferably also involves optical waveguides or fibre-optic waveguide bundles.

Moreover, in the region of the shaft or in the proximal region of the measurement probe, a coupling can be provided here which is used to couple in measurement light from a light source into the light-guiding connection.

This type of refinement is particularly suitable for the use of the measurement probe for reflection measurements. In this case, the light of a light source with a known spectrum is projected onto the process material such that changes in the composition of the process material and the like can be inferred from the change of the spectrum of the reflected light.

Moreover, this type of refinement is also suitable for Raman or fluorescence measurements. In this case, excitation light of a known spectrum is projected via the light exit opening onto the process material, and the apparatus evaluates the scattered light or emission spectrum received through the light entrance opening.

It is particularly preferably provided that the measurement probe is designed for reflection measurements in the NIR range. Pursuant to international agreements, the NIR (near infrared) range is the range of the electromagnetic spectrum between 750 and 2500 nm. This wavelength range is particularly suitable for reflective measurements for substrate composition, since many of the molecules of interest absorb very well in the NIR range.

NIR reflection measurements are therefore very commonplace in the process control in the food industry, and in the chemical and pharmaceutical industries.

The present invention is explained in more detail by means of the figures shown and discussed below. It should be taken into consideration in this context that the figures are only of a descriptive character and are not intended to limit the invention in any way.

BRIEF DESCRIPTION OF THE DRAWINGS

FIG. 1 shows an optical measuring probe.

DETAILED DESCRIPTION OF THE INVENTION

FIG. 1 shows an optical measurement probe 10 for process monitoring with a distal end 11, arranged in the region of a process apparatus whose wall is indicated by dashes, with a light entrance opening 12. The measurement probe 10 also has a proximal end 13, which is coupled, for example, to a spectrometer (not illustrated).

A shaft 14 comprising a light-guiding connection between the distal and proximal ends of the measurement probe is arranged between the two ends. The light-guiding connection is a fibre-optic waveguide or an optical waveguide bundle with a coating and flexible metal reinforcement. The measurement probe has in its distal region 11 relative to the shaft 14 a reduced external diameter.

In this way, the measurement probe provides only a small area for the deposition of contaminations in the region of the process apparatus, and the forces which the moving process material has to exert in order to tear away again any adherent deposits are reduced to the lowest possible level.

Furthermore, the measurement probe has a purging device 15 with a purging duct arranged in the region of the shaft and with a purging opening 16 arranged in the region of the distal end 11.

This purging device can be used to remove, by purging, deposits which adhere despite the reduced area in the region of the distal end of the measurement probe.

Here, suitable purging media are liquids such as water or solvent, gases such as air or inert gases (N2, Ar, Xe) or conveyable solids such as powder or microgranules. It is in particular possible to use as purging medium starting materials, intermediate products or products used in the relevant process.

Moreover, the measurement probe has a dedicated optical waveguide 17 for coupling in measurement light and a plurality of light exit openings 18 arranged around the light entrance opening which is arranged centrally.

The measurement probe can be designed for reflection, Raman, turbidity or fluorescence measurements. In all cases, measurement light of a light source with a known spectrum is radiated via the optical waveguide 17 and the light exit opening onto the process material, and the reflected light or the fluorescence emitted on account of the excitation is received via the light entrance opening 12 and guided via the light-guiding connection to an evaluation device, in particular a spectrometer.

The invention claimed is:

1. Optical reflection measurement probe (10) for process monitoring of a material in a medium, comprising
    a) a distal end (11) with a light entrance opening (12),
    b) a proximal end (13) coupled to an evaluation device,
    c) a rigid sleeve (14) comprising a first light-guiding connection between the distal and proximal ends of the measurement probe, arranged between the two ends, wherein the light guiding connection involves fibre-optic waveguides or optical waveguide bundles without any flexible sheathing and wherein
    (d) the measurement probe has, in its distal region (11) relative to the rigid sleeve (14) and/or the proximal end (13), a reduced external diameter,
    wherein a transition between the rigid sleeve (14) and the distal region is conically shaped for reducing contamination,
    wherein the measurement probe has a purging device (15) with a purging duct arranged in the rigid sleeve (14) and with a purging opening (16) arranged in the distal end, proximate to the light entrance opening,
    wherein the purging duct conveys the same medium as the medium used in the process that is being monitored,
    wherein the purging can be carried out continuously, at fixed intervals or if cleaning is required and
    wherein the purging device creates pulsed purges or high-pressure purges.

2. Optical measurement probe according to claim 1, wherein the measurement probe further comprises
    a) a second light-guiding connection (17) for coupling in measurement light of a light source with a known spectrum
    b) and a light exit opening (18) in the distal region of the measurement probe.

3. Optical measurement probe according to claim 1, wherein the measurement probe is designed for reflection measurements in the NIR range.

4. Optical measurement probe according to claim 1, wherein the reduced diameter of the shaft (14) is about 2.0 mm and the rigid sleeve is about 12 mm.

* * * * *